United States Patent
Nacinovich

(10) Patent No.: US 11,356,446 B1
(45) Date of Patent: Jun. 7, 2022

(54) MEDICAL RECORD DATA CARD

(71) Applicant: Paul Nacinovich, Sparta, NJ (US)

(72) Inventor: Paul Nacinovich, Sparta, NJ (US)

(*) Notice: Subject to any disclaimer, the term of this patent is extended or adjusted under 35 U.S.C. 154(b) by 626 days.

(21) Appl. No.: 16/417,799

(22) Filed: May 21, 2019

(51) Int. Cl.
*H04L 9/40* (2022.01)
*G06F 21/62* (2013.01)
*G06F 16/11* (2019.01)
*G16H 10/60* (2018.01)

(52) U.S. Cl.
CPC .......... *H04L 63/10* (2013.01); *G06F 16/122* (2019.01); *G06F 21/6245* (2013.01); *G16H 10/60* (2018.01)

(58) Field of Classification Search
CPC ....... H04L 63/10; G16H 10/60; G06F 16/122; G06F 21/6245
USPC ............................................................ 726/7
See application file for complete search history.

(56) References Cited

U.S. PATENT DOCUMENTS

| | | | |
|---|---|---|---|
| 8,381,287 B2 | 2/2013 | Trotter | |
| 8,977,572 B2 | 3/2015 | Herlitz | |
| 2004/0267572 A1* | 12/2004 | Emery | G06Q 10/1095 705/2 |
| 2005/0075909 A1 | 4/2005 | Flagstad | |
| 2009/0150292 A1 | 6/2009 | Trinh | |
| 2012/0232929 A1 | 9/2012 | Experton | |
| 2017/0011174 A1 | 1/2017 | Higgs | |
| 2020/0250669 A1* | 8/2020 | Radu | G06Q 20/4014 |
| 2021/0105267 A1* | 4/2021 | Brown | G06F 21/6218 |

FOREIGN PATENT DOCUMENTS

| | | | | |
|---|---|---|---|---|
| CN | 10195199 A | * | 12/2010 | ............ H04W 88/02 |
| CN | 101528117 B | * | 12/2011 | ......... G06F 19/3418 |
| CN | 102819760 A | * | 12/2012 | |
| CN | 102882847 A | * | 1/2013 | |
| CN | 106355004 A | * | 1/2017 | |
| CN | 107360158 B | * | 8/2019 | ............. H04L 63/08 |
| WO | WO-2009006609 A1 | * | 1/2009 | ....... G06F 16/24578 |
| WO | WO-200912658 A2 | * | 6/2009 | ................ H04L 9/32 |
| WO | WO-2009070430 A2 | * | 6/2009 | ........... G06Q 20/223 |

(Continued)

OTHER PUBLICATIONS

Azeta et al., "Implementing a medical record system with biometrics authentication in E-health", IEEE, doi: 10.1109/AFRCON.2017.8095615, 2017, pp. 979-983. (Year: 2017).*

(Continued)

*Primary Examiner* — Peter C Shaw

(57) ABSTRACT

The medical record data card is a smart card. The medical record data card is an electric circuit that is used as a dongle. The medical record data card electrically connects with a logical device. The medical record data card physically authenticates the identity of the cardholder. The medical record data card authorizes access to medical records contained in a medical records database. The medical record data card comprises an authentication device, a medical facility data device, the medical records database, and a communication link. The medical facility communicates with the medical records database using the communication link. The authentication device is the smart card. The authentication device electrically connects to a logical device that enables the access of the medical facility data device to the medical records contained in the medical records database.

17 Claims, 4 Drawing Sheets

(56) References Cited

FOREIGN PATENT DOCUMENTS

| WO | WO-2012067640 A1 | * | 5/2012 | ......... G06K 9/00013 |
|---|---|---|---|---|
| WO | 2016007932 | | 1/2016 | |
| WO | WO-2021066834 A1 | * | 4/2021 | ......... H04L 63/0272 |

OTHER PUBLICATIONS

Sharif et al., "An Efficient Access Privacy Protocol for Healthcare Patient Information System", IEEE, doi: 10.1109/ICCWAMTIP47768.2019.9067602, 2019, pp. 461-465. (Year: 2019).*

Jayabalan et al., "Continuous and transparent access control framework for electronic health records: A preliminary study", IEEE, doi: 10.1109/ICITISEE.2017.8285487, 2017, pp. 165-170. (Year: 2017).*

Mirkovic et al., "Secure solution for mobile access to patient's health care record", IEEE, doi: 10.1109/HEALTH.2011.6026769, 2011, pp. 296-303. (Year: 2011).*

\* cited by examiner

MEDICAL RECORD DATA CARD

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of physics including electric data processing and protecting access to data via a platform using keys, more specifically, protecting medical data on a database. (G06F21/6245)

SUMMARY OF INVENTION

The medical record data card is a smart card. The medical record data card is an electric circuit that is used as a dongle. The medical record data card electrically connects with a logical device. The medical record data card physically authenticates the identity of the cardholder. The medical record data card authorizes access to medical records contained in a medical records database. The medical record data card comprises an authentication device, a medical facility data device, the medical records database, and a communication link. The medical facility communicates with the medical records database using the communication link. The authentication device is the smart card. The authentication device electrically connects to a logical device that enables the access of the medical facility data device to the medical records contained in the medical records database.

These together with additional objects, features and advantages of the medical record data card will be readily apparent to those of ordinary skill in the art upon reading the following detailed description of the presently preferred, but nonetheless illustrative, embodiments when taken in conjunction with the accompanying drawings.

In this respect, before explaining the current embodiments of the medical record data card in detail, it is to be understood that the medical record data card is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the medical record data card.

It is therefore important that the claims be regarded as including such equivalent construction insofar as they do not depart from the spirit and scope of the medical record data card. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
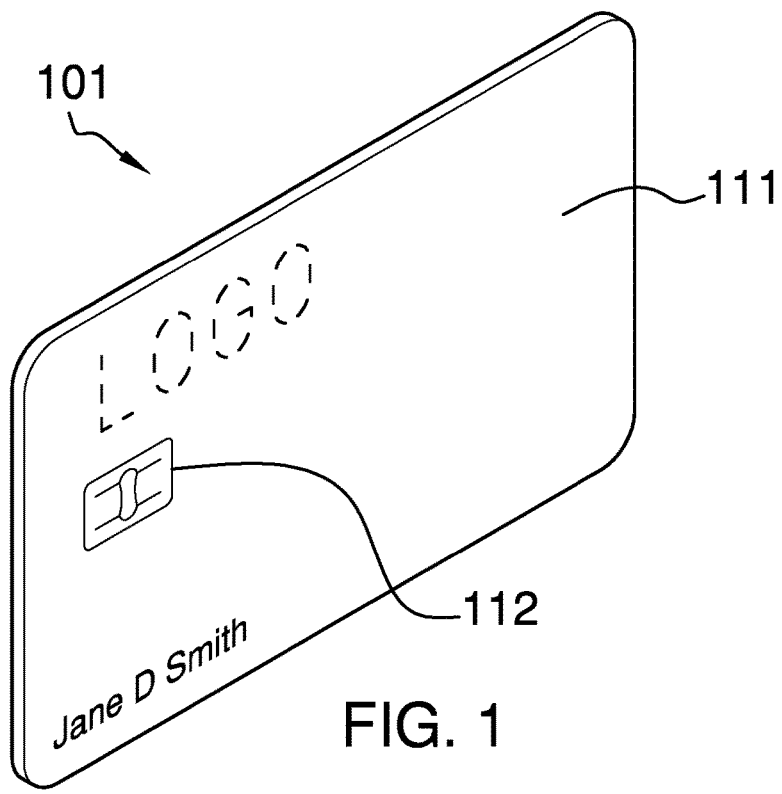
FIG. 1 is a perspective view of an embodiment of the disclosure.
Figure 2:
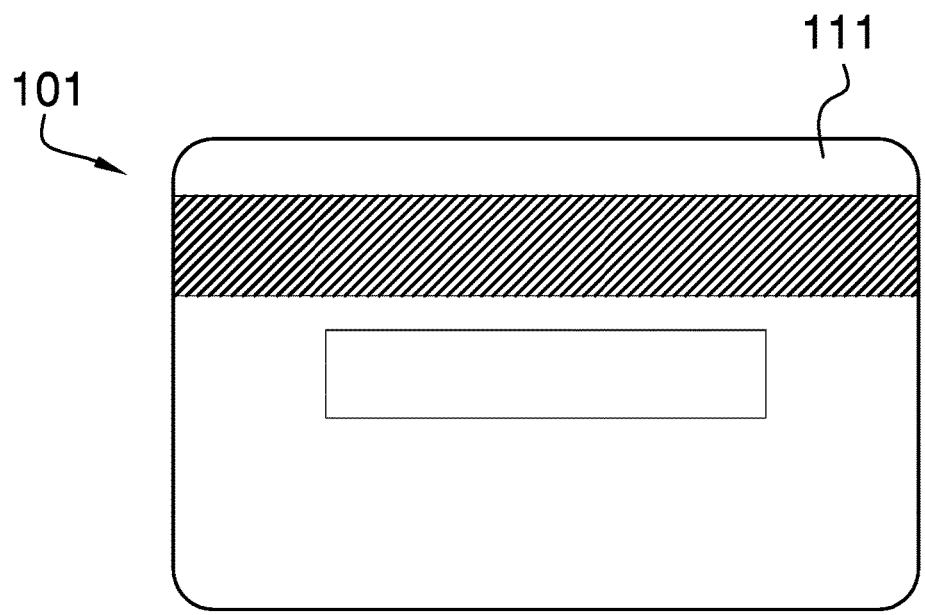
FIG. 2 is a rear view of an embodiment of the disclosure.
Figure 3:
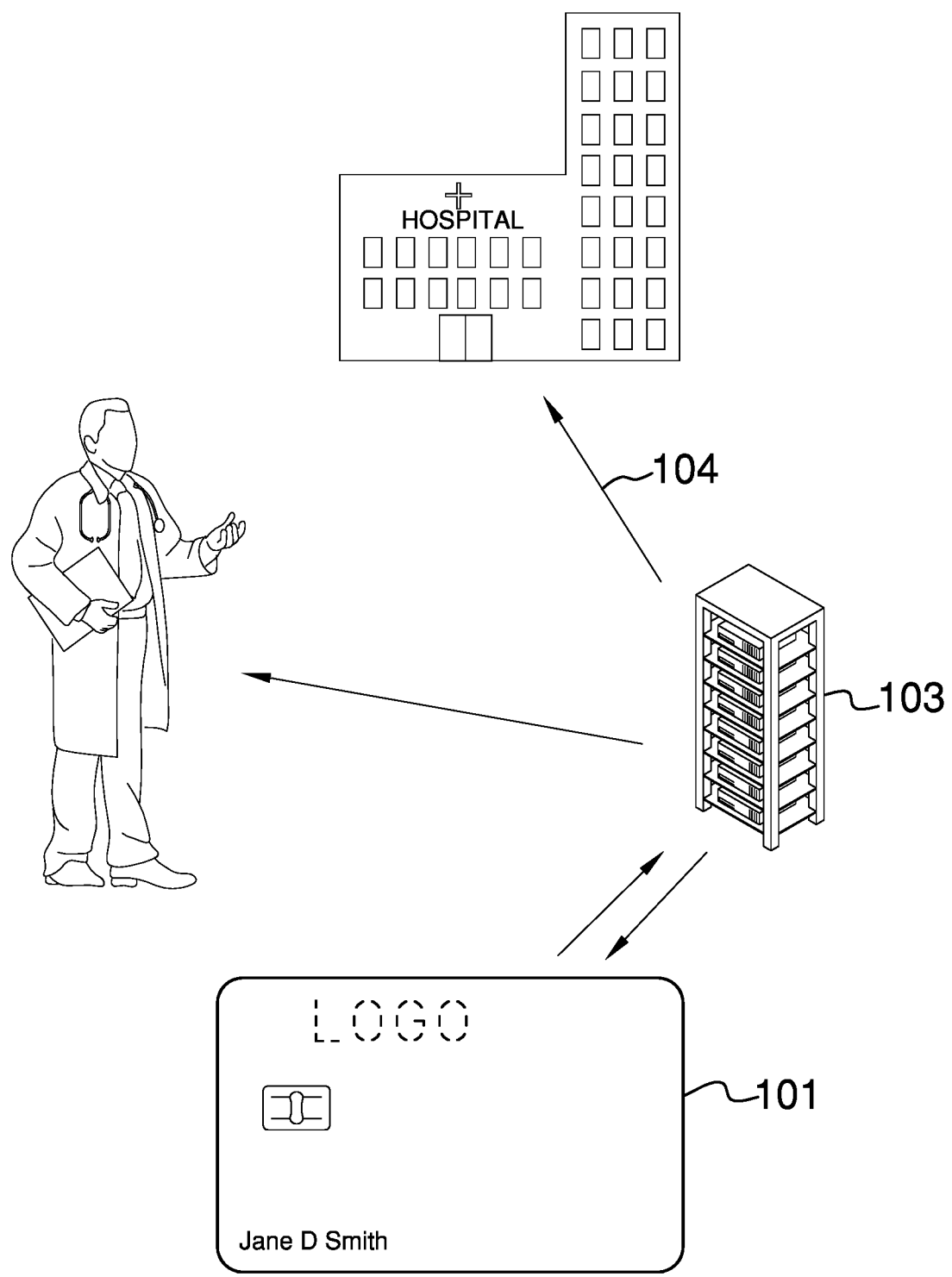
FIG. 3 is an in-use view of an embodiment of the disclosure.
Figure 4:
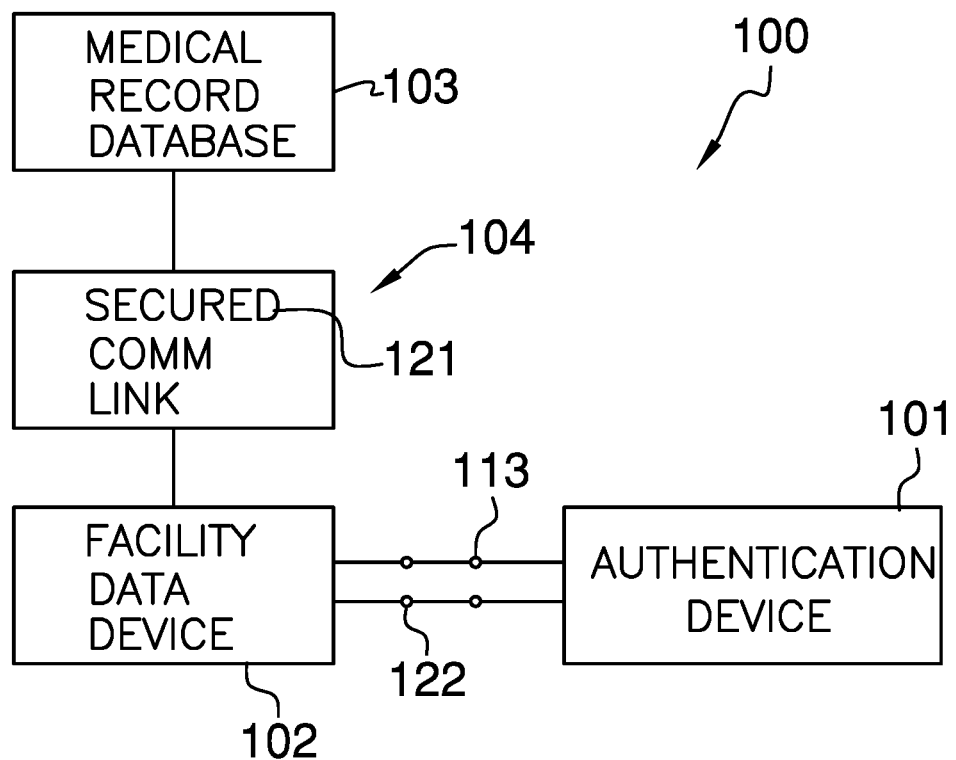
FIG. 4 is a schematic view of an embodiment of the disclosure.
Figure 5:
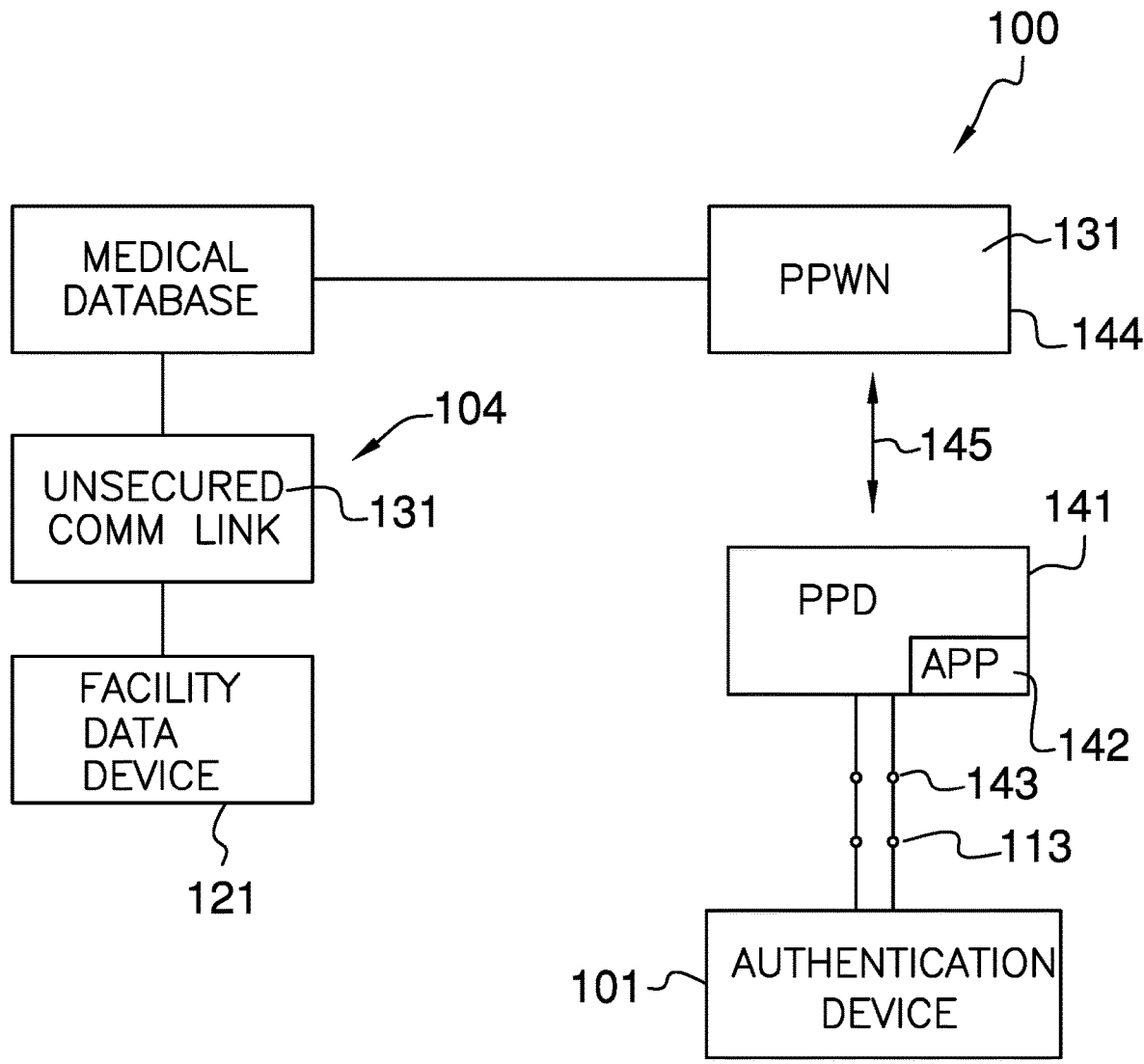
FIG. 5 is an alternate schematic view of an embodiment of the disclosure.

Detailed reference will now be made to one or more potential embodiments of the disclosure, which are illustrated in FIGS. 1 through 5.

The medical record data card 100 (hereinafter invention) is a smart card. The invention 100 is an electric circuit that is used as a dongle. The invention 100 electrically connects with a logical device. The invention 100 physically authenticates the identity of the cardholder. The invention 100 authorizes access to medical records contained in a medical records database 103. The invention 100 comprises an authentication device 101, a medical facility data device 102, the medical records database 103, and a communication link 104. The medical facility data device 102 communicates with the medical records database 103 using the communication link 104. The authentication device 101 is the smart card. The authentication device 101 electrically connects to a logical device that enables the access of the medical facility data device 102 to the medical records contained in the medical records database 103.

The medical facility data device 102 is a logical device. The medical facility data device 102 communicates with the medical records database 103 using the communication link 104. The medical facility data device 102 downloads the medical records of the authorized user from the medical records database 103 after the authorized user has been authenticated.

The medical records database 103 is a collection of medical records that are organized by a medical records personnel. The medical records database 103 is organized such that the medical data is stored in an electronically accessible format. The medical records database 103 is organized such that the medical data can be stored, searched, and retrieved using electronic circuits. The medical records database 103 is maintained on a logical device such that the medical records can be stored, searched, and retrieved by the logical device that forms the medical records database 103.

The authentication device 101 is a credit card 111 sized structure. The authentication device 101 is an EMV smart card. This disclosure assumes that the authentication device 101 is in the custody of an authorized user. The authentication device 101 is a dongle that authenticates the identity of the authorized user. The authentication data provided by the authentication device 101 authorizes the medical records database 103 to release the medical records of the authorized user to the medical facility data device 102. The authentication device 101 comprises a credit card 111, an EMV chip 112, and an access plug 113.

The credit card 111 is a stiff structure formed as a card. The credit card 111 has the standardized dimensions of a credit card 111.

The EMV chip 112 is an electric circuit. The EMV chip 112 contains electrically encoded data used to identify the authorized user of the authentication device 101. The EMV chip 112 authenticates the presence of the authentication device 101 which this disclosure assumes is in the custody of the authorized user. Upon properly receiving the authentication data associated with the EMV chip 112, the medical records database 103 will fulfill data requests made to the medical records database 103 by the appropriate medical facility data device 102.

The access plug 113 is an electrical connection that is formed into the EMV chip 112. The access plug 113 provides an electrical interface that allows the data contained in the EMV chip 112 to be accessed. The access plug 113 is configured such that the authentication device 101 forms a plug that inserts into a port configured to interface with the access plug 113.

The communication link 104 is a structured data exchange mechanism that is established between the medical facility data device 102 and the medical records database 103. The communication link 104 exchanges data between the medical facility data device 102 and the medical records database 103 after the authentication device 101 has been presented for authentication. The communication link 104 is selected from the group consisting of a secured communication link 121 and an unsecured communication link 131.

In the first potential embodiment of the disclosure, the selected communication link 104 is the secured communication link 121. In this first scenario, the medical facility data device 102 further comprises a reader port 122.

The secured communication link 121 is a communication link 104 between the medical facility data device 102 and the medical records database 103. In the secured communication link 121 scenario, the medical facility data device 102: a) interfaces with the EMV chip 112 of the authentication device 101; and, b) transmits the authentication received from the authentication device 101 directly to the medical records database 103 for authentication. Once the authentication device 101 has been authenticated by the medical records database 103, the medical facility data device 102 communicates with the medical records database 103 to receive and update the requested medical records.

The reader port 122 is an electrical device. The reader port 122 is configured to form a port that receives the authentication device 101 for authentication. The reader port 122 forms the electrical connections required to allow the medical facility data device 102 to retrieve the authentication information from the access plug 113 of the EMV chip 112 of the authentication device 101 for processing.

In the second potential embodiment of the disclosure, the selected communication link 104 is the unsecured communication link 131. In this second scenario, the invention 100 further comprises a personal data device 141. The personal data device 141 further comprises an application 142, a PDD port 143, a commercially provided and publicly available cellular wireless network 144, and a wireless communication link 145.

The unsecured communication link 131 is a communication link 104 between the medical facility data device 102 and the medical records database 103. In the unsecured communication link 131 scenario, the medical facility data device 102 does not have the ability to authenticate the information contained in the authentication device 101. The unsecured communication link 131, therefore, establishes a communication link 104 requesting the desired medical records while the personal data device 141 simultaneously contacts the medical records database 103 over an independent communication pathway to provide the authentication information required from the EMV chip 112 of the authentication device 101.

When the medical records database 103 simultaneously receives a data request from a medical facility data device 102 over the unsecured communication link 131 while simultaneously receiving the authentication from the access plug 113 of the authentication device 101 over an independent communication pathway the medical records database 103 presumes that the requested medical records can be released to the medical facility data device 102 over the unsecured communication link 131.

The personal data device 141 is a logical device. The personal data device 141 is a programmable device. The personal data device 141 accepts digital and analog inputs, processes the digital and analog inputs according to previously specified logical processes and provides the results of these previously specified logical processes as digital or analog outputs.

The personal data device 141 is a programmable electrical device that provides data management and communication services through one or more functions referred to as the application 142. The application 142 is a set of logical operating instructions that are performed by the personal data device 141. The addition of an application 142 will provide increased functionality for the personal data device 141. This disclosure assumes that an application 142 exists for the purpose of interacting with the invention 100. Methods to design and implement an application 142 on a personal data device 141 are well known and documented in the electrical arts.

The application 142 controls the operation of the PDD port 143 such that the personal data device 141 can extract the authentication data from the authentication device 101. The application 142 transmits the extracted authentication data received from the authentication device 101 to the commercially provided and publicly available cellular wireless network 144 over the wireless communication link 145.

The PDD port 143 is an electrical device. The PDD port 143 is electrically connected to the personal data device 141. The authentication device 101 plugs into the PDD port 143 such that the personal data device 141 is electrically connected to the access plug 113 of the EMV chip 112 of the personal data device 141.

The commercially provided and publicly available cellular wireless network 144 transmits the extracted authentication data received from the application 142 of the personal data device 141 and transmits the authentication data to the medical records database 103 for processing.

The use of a commercially provided and publicly available cellular wireless network 144 is preferred because: 1) of its low cost; 2) of the widespread availability and the broad interoperability between competing commercially provided and publicly available cellular wireless networks 144; and, 3) methods and techniques to send SMS and MMS messages over a commercially provided and publicly available cellular wireless network 144 are well known and documented by those skilled in the electrical arts.

The wireless communication link 145 is a radio frequency communication pathway formed by the personal data device 141 with the commercially provided and publicly available cellular wireless network 144.

The following definitions were used in this disclosure:

Application or App: As used in this disclosure, an application or app is a self-contained piece of software that is especially designed or downloaded for use with a personal data device.

Card: As used in this disclosure, a card means a flat stiff piece of material that bears information. Typical materials used to make cards include, but are not limited to, heavy paper, cardboard, plastic coated paper, or thin plastic. While this disclosure allows for variations in the size of a card, it is anticipated that cards will approximate the size of a traditional deck of playing cards. The sides of the card that bear the information are called faces.

Commercially Provided And Publicly Available Cellular Wireless Network: As used in this disclosure, a commercially provided and publicly available cellular wireless network refers to subscription-based publically available wireless network commonly used to provide wireless communication access for personal data devices. The commercially provided and publicly available cellular wireless network will typically provide voice communication, data communication services, and SMS and MMS messaging services. The commercially provided and publicly available cellular wireless network is commonly referred to as the cellular network. The commercially provided and publicly available cellular wireless network is abbreviated as the PPWN.

Communication Link: As used in this disclosure, a communication link refers to the structured exchange of data between two objects.

Credit Card: As used in this disclosure, a credit card is a form of identification that enables a person bearing the card to purchase a good or service from a vendor on the basis of credit provided by either the vendor or a third party. The form factor of a credit card is standardized with dimensions of roughly 3.4 inches by 2.1 inches.

Custody: As used in this disclosure, custody refers to an object or person that is under the physical control or care of a custodian. The custodian is an appropriate authority responsible for the proper operation, appropriate use, or well-being of the object or person that is in custody.

Database: As used in this disclosure, a database refers to: 1) a set of data that is organized and stored in a manner that allows for the search and retrieval of data from the data set; or, 2) the electronic device that stores and organizes a data set as described in the first definition.

Dongle: As used in this disclosure, a dongle is a second electrical circuit that plugs into a first electrical circuit. The first electrical circuit and the second electrical circuit are typically housed independently. The operation of the first electrical circuit is influenced by the connection of the second electrical circuit.

Electric Circuit: As used in this disclosure, an electric circuit is a closed loop path through which electrons flow. The closed loop will generally initiate and terminate at an electrical power source.

EMV: As used in this disclosure, EMV stands for Europay Mastercard Visa. The EMV is a standardized form of a smart card wherein an integrated circuit, often referred to as a chip, is mounted within a credit card. The EMV contains within it the identification information necessary to verify that the credit card being used is the one that was originally issued. In the United States (or at least in the southeastern United States) the equipment used to interface with an EMV smart card is often called a "chip reader."

Form Factor: As used in this disclosure, the term form factor refers to the size and shape of an object.

Interface: As used in this disclosure, an interface is a physical or virtual boundary that separates two different systems across which information is exchanged.

Logical Device: As used in this disclosure, a logical device is an electrical device that processes externally provided inputs to generate outputs that are determined from a previously determined logical functions. A logical device may or may not be programmable.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

PDD: As used in this disclosure, PDD is an acronym for personal data device.

Personal Data Device: As used in this disclosure, a personal data device is a handheld logical device that is used for managing personal information and communication. Examples of personal data device include, but are not limited to, cellular phones, tablets, and smartphones. See logical device Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

PPWN: As used in this disclosure, the PPWN is an acronym for a publically provided wireless network. The PPWN refers to a commercially provided and publicly available cellular wireless network.

Roughly: As used in this disclosure, roughly refers to a comparison between two objects. Roughly means that the difference between one or more parameters of the two compared are not significantly different.

Smart Card: As used in this disclosure, a smart card is a logical device. The smart card is a programmable electrical circuit housed in a plastic card that is roughly the size of a credit card. The smart card is commonly used to: a) identify an individual; b) store data associated with the individual; c) communicate with a point of sale terminal; and, d) facilitate financial transactions for the individual through the point of sale terminal.

Wireless: As used in this disclosure, wireless is an adjective that is used to describe a communication channel between two devices that does not require the use of physical cabling.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A medical record access device comprising an authentication device, a medical facility data device, the medical records database, and a communication link; wherein the medical facility data device communicates with the medical records database using the communication link; wherein the authentication device electrically connects to a logical device that enables the access of the medical facility data device to the medical records contained in the medical records database; wherein the medical record access device is a smart card; wherein the medical record access device is an electric circuit; wherein the medical record access device electrically connects with a logical device; wherein the medical record access device authorizes access to medical records contained in a medical records database; wherein the authentication device is the smart card, wherein the communication link is selected from the group consisting of a secured communication link and an unsecured communication link, and wherein when the medical records database simultaneously receives a data request from the medical facility data device over the unsecured communication link while simultaneously receiving the authentication from the access plug of the authentication device over the commercially provided and publicly available cellular wireless network the medical records database releases the requested medical records to the medical facility data device over the unsecured communication link.

2. The medical record access device according to claim 1 wherein the medical facility data device is a logical device; wherein the medical records database is a collection of medical records; wherein the medical records database is organized such that the medical data is stored in an electronically accessible format.

3. The medical record access device according to claim 2 wherein the authentication device is a credit card sized structure; wherein the authentication device is an EMV smart card.

4. The medical record access device according to claim 3 wherein the authentication device is a dongle.

5. The medical record access device according to claim 4 wherein the authentication data provided by the authentication device authorizes the medical records database to release the medical records to the medical facility data device.

6. The medical record access device according to claim 5 wherein the authentication device comprises a credit card, an EMV chip, and an access plug; wherein the EMV chip attaches to the credit card; wherein the access plug attaches to the EMV chip; wherein the credit card is a stiff structure formed as a card; wherein the credit card has the standardized dimensions of a credit card.

7. The medical record access device according to claim 6 wherein the EMV chip is an electric circuit; wherein the EMV chip contains electrically encoded data used to identify the authentication device; wherein the EMV chip authenticates the presence of the authentication device.

8. The medical record access device according to claim 7 wherein upon properly receiving the authentication data associated with the EMV chip, the medical records database will fulfill data requests made to the medical records database by the appropriate medical facility data device.

9. The medical record access device according to claim 8 wherein the access plug is an electrical connection that is formed into the EMV chip; wherein the access plug provides an electrical interface that allows the data contained in the EMV chip to be accessed.

10. The medical record access device according to claim 9 wherein the access plug is configured such that the 1 authentication device forms a plug that inserts into a port configured to interface with the access plug.

11. The medical record access device according to claim 10 wherein the communication link is a structured data exchange mechanism that is established between the medical facility data device and the medical records database; wherein the communication link exchanges data between the medical facility data device and the medical records database after the authentication device has been presented for authentication.

12. The medical record access device according to claim 1 wherein the selected communication link is the secured communication link; wherein the secured communication link is a communication link between the medical facility data device and the medical records database; wherein in the secured communication link scenario, the medical facility data device interfaces with the EMV chip of the authentication device; wherein in the secured communication link transmits the authentication received from the authentication device directly to the medical records database for authentication.

13. The medical record access device according to claim 12 wherein the medical facility data device further comprises a reader port; wherein the reader port is an electrical device.

14. The medical record access device according to claim 12 wherein the reader port receives the authentication device for authentication.

15. The medical record access device according to claim 13 wherein the reader port forms the electrical connections required to allow the medical facility data device to retrieve the authentication information from the access plug of the EMV chip of the authentication device for processing.

16. The medical record access device according to claim 1 wherein the selected communication link is the unsecured communication link; wherein the unsecured communication link is a communication link between the medical facility data device and the medical records database; wherein in the unsecured communication link scenario, the medical facility data device cannot authenticate the information contained in the authentication device; wherein the medical record access device further comprises a personal data device; wherein the unsecured communication link establishes a communication link requesting the desired medical records while the personal data device simultaneously contacts the medical records database over an independent communication pathway to provide the authentication information required from the EMV chip of the authentication device.

17. The medical record access device according to claim 16 wherein the personal data device further comprises an application, a PDD port, a commercially provided and publicly available cellular wireless network, and a wireless communication link; wherein the personal data device is a logical device; wherein the personal data device is a programmable device; wherein the application is a set of logical operating instructions that are performed by the personal data device; wherein the application controls the operation of the PDD port such that the personal data device can extract the authentication data from the authentication device; wherein the application transmits the extracted authentication data received from the authentication device to the commercially provided and publicly available cellular wireless network over the wireless communication link; wherein the PDD port is an electrical device; wherein the PDD port is electrically connected to the personal data device; wherein the authentication device plugs into the PDD port such that the personal data device is electrically connected to the access plug of the EMV chip of the personal data device; wherein the commercially provided and publicly available cellular wireless network transmits the extracted authentication data received from the application of the personal data device and transmits the authentication data to the medical records database for processing; wherein the wireless communication link is a radio frequency communication pathway formed by the personal data device with the commercially provided and publicly available cellular wireless network.

* * * * *